United States Patent
Fabbri et al.

(10) Patent No.: US 8,745,085 B2
(45) Date of Patent: Jun. 3, 2014

(54) SYSTEM FOR EXPLANATION-BASED AUDITING OF MEDICAL RECORDS DATA

(75) Inventors: Daniel Fabbri, Ann Arbor, MI (US); Kristen Lefevre, Ann Arbor, MI (US)

(73) Assignee: The Regents of the University of Michigan, Ann Arbor, MI (US)

( * ) Notice: Subject to any disclaimer, the term of this patent is extended or adjusted under 35 U.S.C. 154(b) by 0 days.

(21) Appl. No.: 13/589,072

(22) Filed: Aug. 17, 2012

(65) Prior Publication Data

US 2013/0046786 A1  Feb. 21, 2013

Related U.S. Application Data

(60) Provisional application No. 61/524,726, filed on Aug. 17, 2011.

(51) Int. Cl.
*G06F 17/30* (2006.01)

(52) U.S. Cl.
USPC .......................................................... 707/776

(58) Field of Classification Search
USPC .......... 707/2, 3, 706, 776; 705/2, 39; 380/277
See application file for complete search history.

(56) References Cited

U.S. PATENT DOCUMENTS

| | | | |
|---|---|---|---|
| 8,578,500 B2 | 11/2013 | Long | |
| 2004/0249676 A1* | 12/2004 | Marshall et al. | 705/2 |
| 2007/0073519 A1 | 3/2007 | Long | |
| 2009/0097654 A1* | 4/2009 | Blake | 380/277 |
| 2011/0066606 A1* | 3/2011 | Fox et al. | 707/706 |
| 2011/0202457 A1* | 8/2011 | Lawrence | 705/39 |
| 2011/0204142 A1 | 8/2011 | Rao | |

OTHER PUBLICATIONS

Agrawal et al., Auditing compliance with a Hippocratic Database, Proceedings of the 30th VLDB Conference, 2004.
Agrawal et al., Fast algorithms for mining association rules, Proceedings of the 20th VLDB Conference, 1994.
Boxwala et al., Using statistical and machine learning to help institutions detect suspicious access to electronic health records, J. Am. Med. Inform. Assoc., 18:498-505 (2011).
Buneman et al., Why and where: A characterization of data provenance, ICDT 2001.
Chandola et al., Anomaly detection: A survey, ACM Computing Surveys 41(3): Article 15 (Jul. 2009).
Chen et al., Detection of anomalous insiders in collaborative environments via relational analysis of access logs, CODASPY 11, San Antonio Texas (Feb. 21-23, 2011).
Cheney et al., Provenance in databases: Why, how, and where, Foundations and Trends in Databases, 1(4):379-474 (2009).
Fabbri et al., PolicyReplay: Misconfiguration-response queries for data breach reporting, Proceedings of the VLDB Endowment, vol. 3, issue 1, pp. 36-47 (2010).
Fabbri et al., Explanation-based auditing, Proceedings of the VLDB Endowment, vol. 5, No. 0 (2011).
Han et al., Mining Frequent Patterns Without Candidate Generation, ACM SIGMOD Conference 2000.

(Continued)

*Primary Examiner* — Etienne Leroux
(74) *Attorney, Agent, or Firm* — Marshall, Gerstein & Borun LLP

(57) ABSTRACT

A system and method is provided for automatically generating explanations for individual records in an access log.

41 Claims, 12 Drawing Sheets

(56) References Cited

OTHER PUBLICATIONS

Kaushik et al., Efficient auditing for complex SQL queries, Proceedings of the ACM SIGMOD International Conference on Management of Data, SIGMOD 2011, Athens, Greece, Jun. 12-16, 2011.

LeFevre et al., Limiting disclosure in hippocratic databases, Proceedings of the 30th VLDB Conference, Toronto, Canada (2004).

Malin et al., Learning Relational Policies from Electronic Health Record Access Logs, J. Biomed. Inform., 44(2):333-42 (2011).

Motwani et al., Auditing SQL queries, Proceedings of ICDE '08 Proceedings of the 2008 IEEE 24th International Conference on Data Engineering, pp. 287-296 (2008).

Newman, Analysis of weighted networks, Phys. Rev. E, 70:056131 (2004).

Rizvi et al., Extending query rewriting techniques for fine-grained access control, SIGMOD 2004, Paris, France (Jun. 13-18, 2004).

Sandhu et al., Role-based access control models, IEEE Computer, 29(2):38-47 (1996).

Sarawagi et al., Integrating association rule mining with relational database systems: alternatives and implications, pp. 343-54, ACM SIGMOD '98 (1998).

Xu et al., Survey of clustering algorithms, IEEE Transactions on Neural Networks, 16(3):645-78 (2005).

\* cited by examiner

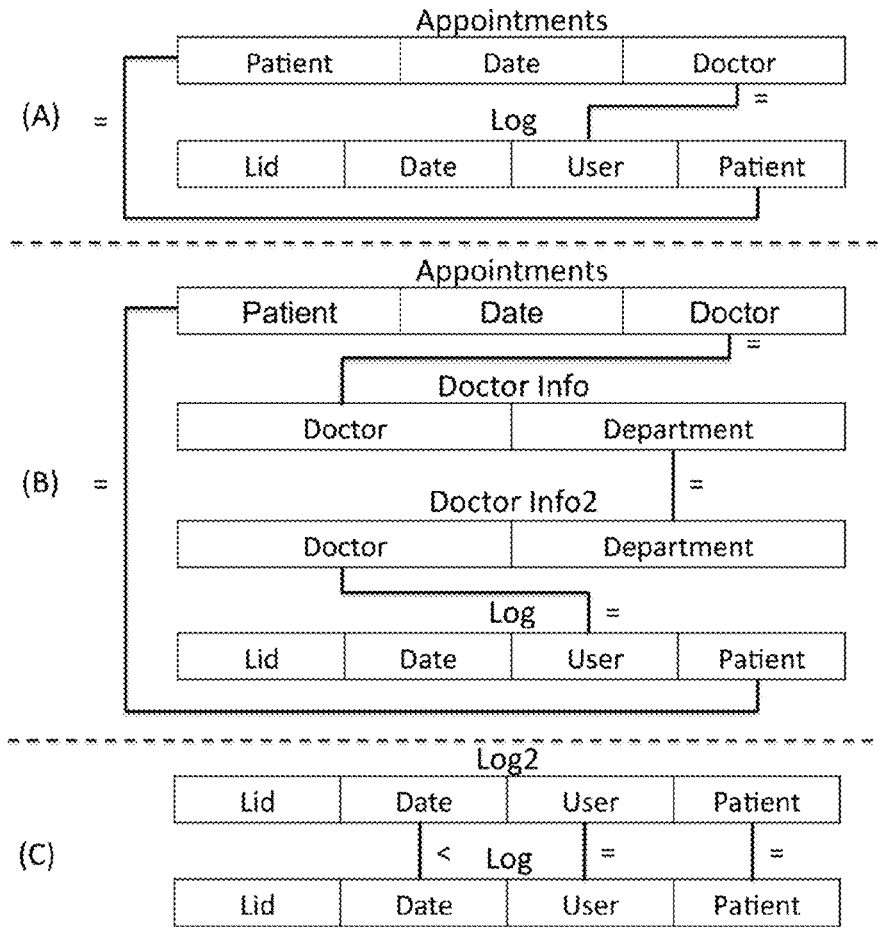
*Figs. 3A, 3B, & 3C*
*Figs. 4A, 4B, & 4C*

Algorithm 1 One-Way Template Mining Algorithm
---
Input: Start attribute (Log.Patient), end attribute (Log.User), support ($S$), max path length ($M$), restricted number of tables referenced ($T$), the set of edges from the schema (Edges) and the database instance ($D$).
Output: Set of supported explanation templates (up to the max length).
 1: Length = 1
 2: Paths = {Edges that begin with the start attribute}
 3: Explanations = { }
 4: while Length $\leq$ M do
 5:    New Paths = { }
 6:    for Path $p \in Paths$ do
 7:       for Edge $e \in Edges$ do
 8:          if areConnected(p, e) then
 9:             Candidate Path = $p.append(e)$
10:             if isARestrictedSimplePath(Candidate Path) then
11:                 if Support(Candidate Path, D) $\geq$ S then
12:                     New Paths.add(Candidate Path)
13:                     if isAnExplanation(Candidate Path) then
14:                         Explanations.add(Candidate Path)
15:    Paths = New Paths
16:    Length += 1
17: Return Explanations

*Fig. 5*

SYSTEM FOR EXPLANATION-BASED AUDITING OF MEDICAL RECORDS DATA

CROSS REFERENCE TO RELATED APPLICATION

The present application claims the benefit of U.S. Provisional Application No. 61/524,726, entitled "System for Explanation-Based Auditing of Medical Records Data", filed on Aug. 17, 2011, which is hereby incorporated by reference herein in its entirety.

FIELD OF TECHNOLOGY

The present disclosure relates generally to databases storing information and, more particularly, to automatically identifying an explanation for user access to stored information.

BACKGROUND

In recent years, laws and regulations have imposed a number of new requirements governing the responsible management of personal and private data. For example, the United States Health Insurance Portability and Accountability Act (HIPAA) stipulates that individuals have the right to request an accounting of the disclosures of their protected health information by hospitals and other healthcare providers (so-called "covered entities").

Most modern electronic health records systems (EHRs) provide the tools necessary to collect access logs automatically. For example, the University of Michigan Health System has built and deployed a web-based clinical EHR called Care-Web. To support compliance with HIPAA, each time an employee accesses a medical record via CareWeb, a record is added to the access log. While the precise format can vary among EHR systems, it is typically quite simple. CareWeb access logs contain four main attributes: Timestamp, User_ID, Patient_ID, and a coded description of the Action performed (e.g., viewed lab reports, or updated history).

One promising approach for supporting HIPAA compliance, and improving overall transparency, is the idea of user-centric auditing. Basically, the idea is to construct a portal where individual patients can login and view a record of all accesses to their medical records. When the underlying access logs are of the form described above, this is relatively straightforward. Unfortunately, the resulting access histories are often long and hard to analyze. Worse, the list of accesses often includes accesses by many people the patient does not know. For example, the patient probably knows the name of his primary care physician, but he is not likely to recognize the name of the intake nurse or the radiologist who read his x-ray.

SUMMARY

Provided herein are techniques for automatically generating explanations for individual records in an access log. The techniques may be used in user-centric auditing applications and provide a novel approach to misuse detection, among other purposes and advantages. A framework for modeling explanations has been developed based on a fundamental observation: For certain classes of databases, including EHRs, the reason for most data accesses can be inferred from data stored elsewhere in the database. For example, if Alice has an appointment with Dr. Dave, this information is stored in the database, and it explains why Dr. Dave looked at Alice's record. Large numbers of data accesses can be explained using general forms called explanation templates.

Rather than requiring an administrator to manually specify explanation templates, a set of algorithms for automatically discovering frequent templates from the database (i.e., those that explain a large number of accesses) is provided. Techniques are described for inferring collaborative user groups, which can be used to enhance the quality of the discovered explanations. The techniques have been evaluated using an access log and data from the University of Michigan Health System. The results demonstrate that the present techniques can provide explanations for over 94% of data accesses in the sample log.

One approach to providing explanations would require the user (e.g., the doctor) to enter a reason each time he accesses a medical record. However, this places an unrealistic burden on the users. Instead, the present techniques provide a way to automatically produce informative explanations.

Furthermore, if there are accesses for which the techniques are not able to generate explanations, in these cases, if the access appears suspicious, the patient may have the right to report the access to the hospital compliance office, and to request an investigation. Either way, developing a system to generate explanations automatically is useful both for the purpose of informing patients how their medical records are being used and for reducing the burden on the compliance office in handling complaints.

Interestingly, the present techniques also provide for a secondary application of explanations for the purpose of automated misuse detection. One approach to securing electronic health records relies on administrators to specify detailed access control policies up-front, and prevents misuse by proactively enforcing these policies. Unfortunately, in environments like hospitals, it is extraordinarily difficult to specify and maintain detailed access control policies. For example, residents and medical students change departments as often as once a week. In fact, overly restrictive policies can have disastrous consequences, interfering with patient care.

Instead, rather than preventing data access, hospitals often err on the side of maintaining a log in hopes of detecting misuse after the fact. Unfortunately, there are few technical tools for proactively detecting misuse from the access log. Common approaches often involve manual analysis, in response to a complaint. Another common strategy is to manually monitor accesses to the records of VIPs (high-profile people). Of course, manual analysis does not scale to the access logs collected by modern hospitals. (For example, in just one week, the University of Michigan Health System collected over 4 million access log records via CareWeb.)

On the other hand, by automatically constructing explanations for why accesses occurred, the present techniques can use this information to reduce the set of accesses that must be examined to those that are unexplained. While one may not be likely to be able to explain every access, the present techniques significantly reduce the set of records that are potentially suspicious.

The present techniques include automatically analyzing individual log records (accesses) in an access log to explain those entries for consumption by a computer system and/or a user. The techniques are constructed, in some examples, on the recognition that for certain classes of databases, including those used to store EHR data, there is typically an identifiable reason for each access. Further, this reason can often be gleaned from information stored elsewhere in the database.

In one embodiment, a method for identifying an explanation for a user access to medical records, includes: accessing, using a computer system, a template database containing a plurality of explanation templates; accessing, using the computer system, log data stored in an access log database and identifying the user access to the medical records; automatically mining, using the computer system, the plurality of explanation templates to identify candidate explanation templates based on the log data; extracting, using the computer system, an explanation corresponding to the user access, based on the candidate explanation templates; and storing the extracted explanation.

In some embodiments, mining the explanation templates identifies a set of frequently used explanation templates as the candidate explanation templates.

In some embodiments, mining is performed based on template type.

In some embodiments, mining is performed based on the lengths of explanation templates.

In some embodiments, mining is performed based on the number of tables used to construct the log data stored in the access log database.

In some embodiments, mining is performed based on the amount of data in the access log database.

In some embodiments, mining is performed using a one-way algorithm.

In some embodiments, mining is performed using a two-way algorithm.

In some embodiments, the method further includes inferring missing data from the log data and automatically mining the plurality of explanation templates to identify the candidate explanation templates based on the log data and the inferred missing data.

BRIEF DESCRIPTION OF THE DRAWINGS

FIGS. 3A-3C illustrate paths through an explanation graph used to analyze an access log, in accordance with an example.

FIGS. 4A-4C illustrate example hospital database and log of access, in accordance with an example.

FIG. 5 illustrates an example one-way algorithm, in accordance with an example.

DETAILED DESCRIPTION

Generally, techniques described herein provide a novel approach to modeling explanations of user interactions with medical records and, in some examples, medical data more generally. The explanations can be viewed as a connection from the data accessed (e.g., about the Patient), through the database, and back to the user who accessed the data (e.g., to the User). Before explanations can be used for user-centric auditing or misuse detection, they must be generated or specified. Our empirical study indicates that most accesses can actually be explained using a limited number of explanation types or templates. For example, the fact that a patient had an appointment with the user who accessed his record is a general explanation type that can explain many different accesses.

While embodiments are described in reference to automatically explaining accesses to medical records, the present system may be used to automatically explain accesses to other types of data, including government records data, credit card data, corporate records, etc.

Example 1.1

Figure 1:
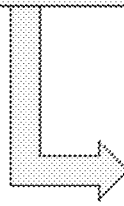
FIG. 1 illustrates a sample access log and resulting explanation.

Consider a patient Alice who is using a user-centric auditing system. She logs into the patient portal and requests a log of all accesses to her medical record. The resulting log is shown in FIG. 1, and includes accesses by four different hospital employees. Looking at this log, Alice would like to understand the reason for each of these accesses. The present techniques, therefore, may provide an explanation for each access; if Alice clicks on a log record, she should be presented with a short snippet of text explaining the access (as illustrated in FIG. 1):

L100 Nurse Nick works with Dr. Dave, and Alice had an appointment with Dr. Dave.

L116 Alice had an appointment with Dr. Dave.

L127 Radiologist Ron reviewed Alice's x-rays for Dr. Dave.

L900 Surgeon Sam performed a surgery for Alice after Dr. Dave referred Alice to Sam.

The present techniques are able to remove some of the burden from the administrator in specifying explanation templates. The techniques include algorithms for automatically discovering templates that occur frequently in a given database (i.e., that explain a large number of accesses). In some examples, the techniques are able to infer missing data so that more accesses can be explained. For example, we observe that databases such as CareWeb are often missing information that is useful for the purpose of constructing explanations. For example, Dr. Dave and Nurse Nick work together, but this information is not recorded anywhere. The inference of data allows for explanations to still be formed.

As discussed below, an extensive empirical study and experimental evaluation was performed using data from CareWeb, which contains over 4.5 million accesses as well as records of appointments, visits, documents produced, and other information. Our experiments confirm the hypothesis that there is a reason for most accesses in our log, and that these accesses can be explained using data located elsewhere in the database. Further, the experiments indicate that (i) common explanation templates can be mined automatically, (ii) missing data can be added to the database to improve the rate at which accesses are explained without producing a significant number of false positives, and (iii) the explanations discovered can explain over 94% of accesses in the log.

Figure 2:
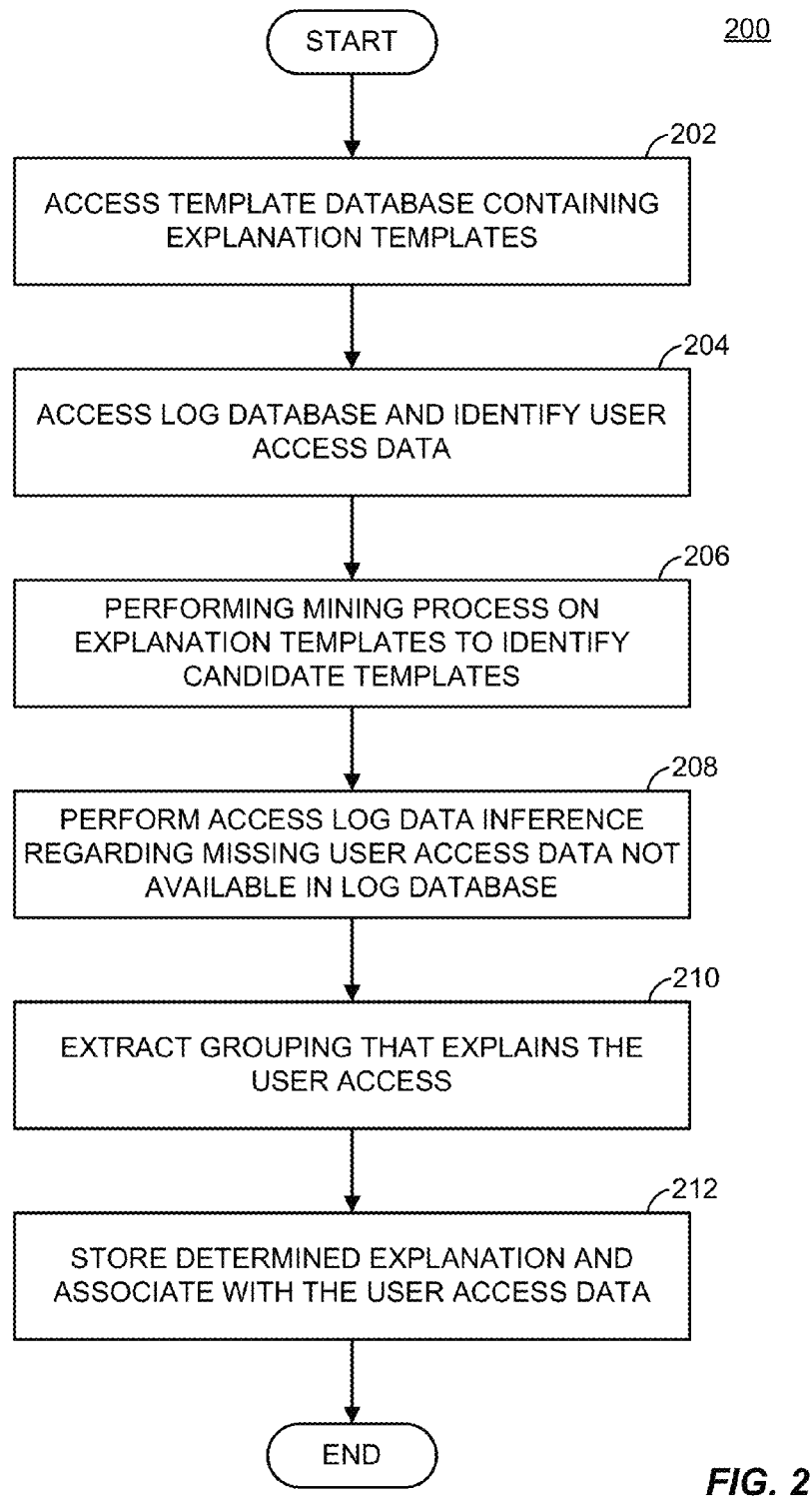
FIG. 2 illustrates an example process for explanation-based auditing in accordance with an example.

To provide an example embodiment of the present techniques, FIG. 2 illustrates a method 200 for explanation auditing. Initially, at a block 202, one or more Explanation Templates are accessed by a computer system, e.g., a local computer or remote computer, where the Explanation Templates, as discussed further below, are tools that can be used to explain many individual accesses. The computer system then accesses user interaction data with medical records, at a block 204. The user interaction data may be collected real time during interaction or may be collected from stored user interaction, e.g., stored on an access log of a local computer or an access log on one or more remote computers. At a block 206, the user data is compared against the Explanation Templates in a mining process, for example, which may be a one-way mining algorithm process, 2 way mining algorithm process, or some other mining process. At a block 208, in the illustrated example, an inference process is performed to identify any missing data to complete the Explanation Template and explanation extraction. At a block 210, an extraction is performed to produce a grouping that explains the user interaction, which is then stored and/or displayed on the computer system or some other remote computer system. At a block 212, the grouping is stored in a database and associated with the user access to be displayed to a subsequent user who accesses the user access data.

Explaining Accesses

Given an entry in an access log, which describes both the data that was accessed (e.g., the patient's medical record) and the user who accessed the data, the present system is able to construct a simple explanation describing the reason for the access. In addition, in at least some examples, an explanation should satisfy the following basic properties:

Human Interpretable: The reason why the access occurred should be easily understood. Among other things, in some examples, an explanation should be logical and Boolean (either it explains the access or not). In contrast, systems that provide probability distributions or other ambiguity are difficult to interpret.

General: Explanations should take on a general form whereby a single explanation type or template explains many accesses by many users. For example, a patient having an appointment with the doctor who accesses his medical record is a common explanation template that can be used to explain many different accesses in the log.

Concise: The explanation should be represented concisely.

Easy to produce/calculate: Given a particular access, it should be easy to compute the explanation(s) for the access.

Explanation Templates

In some examples, a computer system constructs the Explanation Templates. For example, the techniques may start with formalizing the structure of explanations, which can be used to describe why individual accesses occurred. We model an explanation based on the hypothesis that for every legitimate data access, there is a reason for the access, and in most cases the reason for the access can be gleaned from information stored elsewhere in the database.

Example 2.1

Consider the patients Alice and Bob, who log into the patient portal of their healthcare provider's electronic medical records system. To support transparency, the portal allows the patients to view a log of hospital employees who have accessed their records. Among others, the patients observe that an employee named Dave accessed their medical records. While this information may be useful, oftentimes it is important to provide further details, explaining why Dave accessed the record. Consider the following possible explanations:

A. Dave accessed Alice's medical record because Alice had an appointment with Dave on Jan. 1, 2010.

B. Dave accessed Bob's medical record because Bob had an appointment with Mike on Feb. 2, 2010, and Dave and Mike work together in the Pediatrics department.

C. Dave accessed Alice's medical record because Dave previously accessed Alice's record.

D. Dave accessed Alice's medical record because Alice has an appointment with someone else.

Intuitively, an explanation should connect the user who accessed the data with the data itself (i.e., the patient's medical record). In examples (A-C), there is a connection from the user who accessed the data (Dave), through the data in the database (appointment and department information), back to the data that was accessed (Alice or Bob's medical record). In contrast, the final explanation does not provide a connection between the user and the data. Consequently, the final explanation does not provide a meaningful description of why Dave in particular accessed Alice's record.

To capture this intuition more formally, the techniques are able to model the explanation as a path through the database, beginning and ending in the log. We assume that the database stores a log of accesses, which records the time of the access, the user who accessed the data (Log.User) and a reference to the data that was accessed (Log.Patient).

Example Descriptor 1

Explanation Template

An explanation template is a tool that can be used to explain many individual accesses. An explanation template is a stylized query on the database and log. Consider a query Q of the following form, where $T_1, \ldots, T_n$ are (not necessarily distinct) tables in the database, and each $C_i$ is an attribute comparison condition of the form $A_1 \theta A_2$ where $\theta \in \{<, \leq, =, \geq, >\}$.

SELECT Log.Lid, A_1, . . . , A_m

FROM Log, T_1, . . . , T_n

WHERE C_1 AND . . . AND C_j

Let G be a graph, where each attribute in Log, $T_1, \ldots, T_n$ is a node. Let there be an edge from attribute $A_1$ to $A_2$ in G if (i) $A_1$ and $A_2$ are in the same tuple variable (i.e., Log, $T_1, \ldots, T_n$) or (ii) Q imposes a comparison condition between $A_1$ and $A_2$.

Query Q is an explanation template if there is a path P on G that starts at the data that was accessed (Log.Patient) and terminates at the user who accessed the data (Log.User), touching at least one attribute from each tuple variable mentioned in the query, and where no edge is traversed more than once.

Because an explanation template is a query, it can be used to explain why many different data accesses occurred. We refer to these data-specific descriptions (query results) as explanation instances. Notice that instances of a particular explanation template can be easily converted to natural language by providing a parameterized description string.

Example 2.2

Consider the database and log provided in FIG. 4. Explanations like example (A) from Example 2.1 can be derived from the following explanation template:

SELECT L.lid, L.Patient, L.User, A.Date
FROM Log L, Appointments A
WHERE L.Patient=A.Patient
  AND A.Doctor=L.User FIG. 3A shows the graph G associated with this explanation template. Notice that there is a path P that starts at Log.Patient and terminates at Log.User. The edges between attributes in the same table are implicit.

Instances of this explanation template can easily be converted to natural language using a simple description string: "[L.Patient] had an appointment with [L.User] on [A.Date]." For example, log record L1 can be explained using the description "Alice had an appointment with Dave on Jan. 1, 2010."

Explanations like example (B) from Example 2.1 can be derived from the following explanation template:

SELECT L.lid, L.Patient, L.User, A.Doctor, A.Date, I1.Department
FROM Log L, Appointments A, Doctor_Info I1, Doctor_Info I2
WHERE L.Patient=A.Patient
  AND A.Doctor=I1.Doctor
  AND I1.Department=I2.Department
  AND I2.Doctor=L.User FIG. 3B shows the graph associated with this explanation template. Instances of this explanation are easily expressed in natural language: "[L.Patient] had an appointment with [A.Doctor] on [A.Date], and [L.User] and [A.Doctor] work together in the [I1.Department] department."

Notice that a single log record may have multiple explanation instances, generated from one or more explanation templates. For example, the query implementing explanation (A) would produce multiple results with Lid=L1 if Alice had multiple appointments with Dave. We consider each of these instances to be a valuable source of information; in practice, when there are multiple explanation instances for a given log record, we convert each to natural language, and provide a scrolling box containing all of the explanations, ranked in ascending order of path length.

It is useful to draw a further distinction between what we will call simple explanation templates and their more complex decorated counterparts.

Example Descriptor 2

Simple Explanation Template

Consider an explanation template and its associated graph G and path P. The explanation template is simple if it is not possible to remove any set of selection condition edges from G and still have a path P' from Log.Patient to Log.User Intuitively, a simple explanation provides a minimal connection between the data and the user who accessed it. Notice that explanation templates (A) and (B) in Example 2.2 are both simple.

At the same time, simple explanations may not always be sufficient to express the desired semantics. For example, suppose we want to express the idea that an access occurred because the same user previously accessed the data (e.g., explanation (C) in Example 2.1). A simple explanation template could partially capture the desired semantics as follows:

SELECT L1.Lid, L1.Patient, L1.User
FROM Log L1, Log L2
WHERE L1.Patient=L2.Patient
  AND L2.User=L1.User However, to express the temporal aspect of the explanation, we also need the additional selection conditionL1.Date>L2.Date. FIG. 3C shows the graph associated with this explanation template. As a result, this decorated explanation always explains a subset of the accesses that are explained by the corresponding simple explanation.

Example Descriptor 3

Decorated Explanation Template

A decorated explanation template is a simple explanation template with additional selection conditions added.

Finally, for modern databases with large schemas, the number and complexity of explanation can be very large, even if we only consider simple explanations. At the same time, we hypothesize that most explanations only require information from a few tables in the database. For this reason, the system may restrict the number of tables that a path can reference to an administrator-specified value T.

Example Descriptor 4

Restricted Explanation Template

A restricted simple explanation template is a simple explanation template that only refers to at most T tables.

Any of these EXAMPLE DESCRIPTORS may be used to define and determine Explanation Templates accessed in FIG. 1.

Mining Explanations

Before explanations can be used in any particular database, the appropriate explanation templates must be specified. One approach would require the security or database administrator to specify appropriate explanation templates manually. However, this can be a tedious process. Worse, due to the complexity of modern database schemas, a single administrator may not have complete knowledge of all the different reasons that data accesses occur.

While it is important to keep the administrator in the loop, the present system is able to reduce the administrator's burden by automatically suggesting templates from the data. To do that, the templates from a given database are mined. The administrator can then review the suggested set of templates before applying them, or the system may automatically apply the mined templates.

The goal of the mining algorithms is to find the set of frequently used explanation templates, or those that can be used to explain many accesses. Intuitively, this reduces the possibility of spurious results. The problem of mining frequent explanation templates is related to previous work on frequent pattern mining. Indeed, in some examples, our algorithms take a bottom-up pruning approach inspired by algorithms like a priori. There are several important differences between the template mining problem and frequent pattern mining. First, we are mining connected paths between a start and end attributes in the schema. Second, our measure of frequency (support) is different; for explanation templates, frequency is determined by the number of accesses in the log that are explained by the template, so every path we consider must reference the log. Finally, the data is stored across multiple tables in the database, rather than in a single large file of transactions.

Mining Problem Statement

A goal of the system, in some examples, is to find the set of explanation templates that occur frequently in a given database instance. We define support to be the number of accesses in the log that are explained by the template.

An extremely naive approach would enumerate all possible templates of the form described in EXAMPLE DESCRIPTOR 1. However, the number of possible templates is unbounded. Even if the system is restricted to simple templates without self-joins, the number of possible templates is still exponential in terms of the number of attributes in the schema.

To reduce the space, the system may be designed to make some practical simplifying assumptions. (1) The system may only consider simple explanation templates. (2) The system may only consider equi-joins between two tables if there exists a key-foreign key relationship, or if another relationship between two attributes is explicitly provided by the administrator. (3) An attribute and table can only be used in a self-join if the administrator explicitly allows the attribute to be used in a self-join. (4) The system may restrict the path length to M and restrict the number of tables referenced to T. When self-joins are included, a simple explanation's path length is at most min(M, T+#self joins). The system may leave the task of developing algorithms for mining more complex (decorated) explanation templates to future work.

Example Descriptor 5

Explanation Mining

Given a database D and a log of accesses L, return those explanation templates of length at most M, that reference at most T tables and that explain (support) at least s % of the accesses in the log, where the edges in that path are restricted to attributes from the table, key relationships, specified self-joins, or administrator-specified relationships.

Example 3.1

Continuing with Example 2.1 and the database in FIG. 4, template (A) has support of 50% (from access L1), and template (B) has support of 100% (from accesses L1 and L2).

Example One-Way Algorithm

We begin by describing a basic algorithm for mining explanations. An example one-way mining algorithm as may be applied by the system is shown in FIG. 5.

The administrator provides the start attribute Log.Patient (the data that is accessed), the end attribute Log.User (the user who accessed the data), the minimum support S, the maximum length M, the maximum number of tables referenced T, the schema, and the database. We restrict the set of edges that can be used in explanations as described above. An initial set of paths of length one are created by taking the set of edges that begin with the start attribute Log.Patient. The goal of the algorithm is to find the set of supported explanation templates, which are those templates that explain at least s % of the accesses.

As implemented by the system, the one-way algorithm finds the set of supported templates as follows. For each path at the current length and for each edge, the algorithm tests if the two are connected. Intuitively, the path and edge are connected if the last attribute in the path is the same attribute as the first attribute in the edge. Second, for those connected paths and edges, the path and edge are combined by appending the edge to the right end of the path. Third, the algorithm checks if this candidate path is a restricted simple path. Intuitively, the candidate path is simple if it begins at the log and continues to join with previously unvisited tables until the log is reached; the path traverses each node at most once and at most two nodes per table (nodes from self-joins are considered to be from different tables). The candidate path is a restricted simple path if it references no more than T tables (a path that references the underlying table and a self-join for that table are counted as a single reference). Next, the candidate path is converted to SQL and evaluated on the database to calculate the path's support. We calculate the support using the following query:

SELECT COUNT(DISTINCT Log.lid)
FROM Log, T_1, . . . , T_N
WHERE C

If the support is greater than or equal to S=|Log|×s %, then the path is added to the set of new paths that will be used in the next iteration of the algorithm. Furthermore, if the path has the appropriate start and end attributes, then the path is also an explanation template, and is marked accordingly. The algorithm repeats for paths of increasing length until the maximum path length is reached.

Example 3.2

Consider the database shown in FIG. 4; in an example of the system, the one-way algorithm works as follows: The input set of edges includes key-foreign key equi-joins such as {Log.Patient=Appointments.Patient, Appointments.Patient=Log.Patient, Log.User=Appointments.Doctor, Appointments.Doctor=Log.User} and administrator-provided self-joins {Doctor_Info.Department=Doctor_Info2.Department}. The initial set of paths is: {Log.Patient=Appointments.Patient}. This first path is converted into SQL and has the selection conditionLog.Patient=Appointments.Patient and is evaluated on the database. The path has a support of 100%.

Next, connected edges are appended onto the path. For example, one candidate path would have the selection condition: Log.Patient=Appointments.Patient AND Appointments.Doctor=Log.User. This candidate path is also an explanation since it has the correct start and end attributes. The explanation has 50% support.

In some examples of the system, the one-way algorithm works in a bottom-up manner to find the supported explanation templates. There may be several noticeable properties of the algorithm: First, in some examples, the paths always include an attribute from the Log in order to calculate the support for the path; if there was no Log attribute, then it would be impossible to count the number of log entries explained.

Second, in some examples, the support function may be monotonic. If a path P of length l−1 does not have the necessary support (i.e., does not explain s % of the accesses in the log), then adding additional edges to the path will never produce an explanation template with the necessary support. Thus, the bottom-up algorithm is able to prune certain paths that are guaranteed not to have the necessary support.

Performance Optimizations of Example One-Way Algorithm

The system may apply a number of performance optimizations on the one-way algorithm, of which three performance optimizations are described:

Caching Selection Conditions and Support Values: Multiple paths may have the same selection conditions, even though the paths traverse the explanation graph in different manners. Because the order in which the selection conditions are applied does not change the result, these paths are guaranteed to have the same support (i.e., R.attr=T.attr is equivalent to T.attr=R.attr). Thus, a simple optimization for the system is to cache the support of each path that has already been tested. Then, before the next path's support is calculated, the algorithm checks if some variation of the path (with an equivalent selection condition) has already been tested. If so, the algorithm does not need to evaluate the query on the database and can use the previously recorded support value instead.

Reducing Result Multiplicity: The multiplicity of data in the database can impact performance. For example, from Example 2.2, if Alice had three appointments with Dr. Dave, then there would be three instances of explanation (A) for the same log id. These additional rows in the output make computing the support (i.e., the distinct set of log ids) more costly. Therefore, because it does not matter how many times a given log id is in the result, the performance can be improved by reducing the number of rows in the result. To remove duplicates from each table, the system may use a subquery to extract the distinct set of rows from the table, while only projecting those attributes needed for the path. For example, the query from Example 2.2 can be rewritten as follows:

SELECT COUNT(DISTINCT L.lid) FROM Log L,
      (SELECT DISTINCT Patient, Doctor
      FROM Appointments) A
    WHERE L.Patient=A.Patient
      AND A.Doctor=L.User Skipping Non-Selective Paths: For many (short) paths, the selection conditions are not selective and return most of the log. Computing the support for these paths wastes time because these nonselective paths typically have sufficient support and are not pruned. Therefore, the algorithm's performance can be improved by passing these nonselective paths directly to the next iteration of the algorithm, instead of calculating their support. The system may determine if a path is likely to have sufficient support by querying the database optimizer for the number of log ids it expects to be in the result of the query. If the value is greater than the desired support S×c (where c is a constant like 10), the system skips this path and adds it to the set of paths to try in the next iteration of the algorithm. In the special case when the path is also an explanation, the path is not skipped. The constant c is used to account for the optimizer's estimation error. Using this optimization, the system trades off pruning some paths in order to not have to calculate the support of the nonselective paths. Even in the worse case when the database optimizer significantly errs with its estimation, the output set of explanation templates does not change because paths are not discarded; rather, they are tested in the next iteration of the algorithm.

Example Two-Way Algorithm

The one-way algorithm is initiated with the set of paths that begin with the start attribute, and then extends each path to the right until the end attribute is reached. In addition to the paths the one-way algorithm is initiated with, the two-way algorithm's initial paths include those edges that terminate with the end attribute. These paths that terminate with the end attribute are then extended to the left by adding connected edges until the start attribute is reached. Intuitively, the algorithms constructs path in two directions: from the start to the end, and from the end to the start. The two-way algorithm increases the number of paths that are explored. However, in some examples, this added complexity can be leveraged for an optimization.

Bridging Paths for the Example Two-Way Algorithm

The one-way and two-way algorithms explore all paths that have the desired support. However, the goal of the algorithm is to find supported explanation templates. Therefore, by enforcing the constraint that paths must start and end with particular attributes, the algorithm can restrict the set of paths the algorithms must consider. Moreover, since we have paths extending from the start and end attributes from the two-way algorithm, we can combine, or bridge, these paths.

Figure 6:
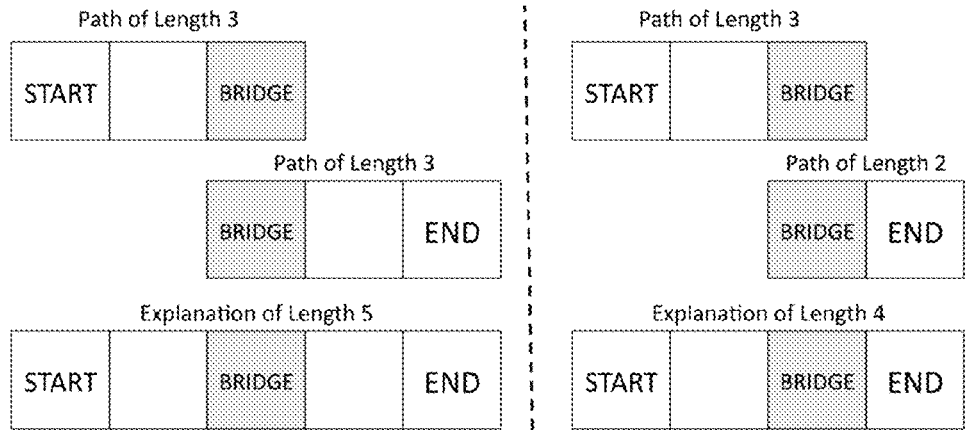
FIG. 6 illustrates bridging paths to create an Explanation, in accordance with an example.

Consider the case that the two-way algorithm has executed and produced all supported paths up to length l. The algorithm can use these paths to easily construct the set of candidate explanation templates up to length 2l−1 (the candidate templates are a superset of those templates that have the necessary support). These candidate templates can be produced by connecting those paths with the start attribute to those paths that terminate with the end attribute as shown in FIG. 6. The remaining paths that do not start or end with one of these attributes can be ignored.

More concretely, for candidate templates of length n ($2 \leq l < n \leq 2l-1$) can be produced by taking paths of length l that begin with the start attribute and connecting them to paths of length n−l+1 that terminate with the end attribute. The paths are bridged because the algorithm may require that the edge where the two paths are connected (the bridge edge) are equivalent. As a result, the length of the combined path is one less than the sum of the individual path lengths. Once the set of candidate templates is produced, the support for each candidate is tested.

Example 3.3

Template (B) from Example 2.1 can be created by bridging the following two paths:

SELECT COUNT(DISTINCT L.lid)
    FROM Log L, Appointments A, Dept_Info I1, Dept_Info I2
    WHERE L.Patient=A.Patient
      AND A.Doctor=I1.Doctor
      AND I1.Department=I2.Department
    SELECT COUNT(DISTINCT L.lid)
    FROM Log L, Dept_Info I1, Dept_Info I2
    WHERE I1.Department=I2.Department
      AND I2.Doctor=L.User Notice that the combined path has the appropriate start and end attributes, and the condition I1.Dept=I2.Dept can be used to bridge the paths.

When the length of the desired path is greater than or equal to 2l, the candidates cannot be constructed from the paths that have been found thus far. While the algorithm can still use the paths to restrict the ends that the candidate template can take, the algorithm does not have knowledge about which edges should be included in the middle of the explanation. Thus, the algorithm must consider all combinations of edges from the schema to bridge these paths.

Bridging paths is beneficial because it can greatly reduce the space of candidate templates to test. In general, since the algorithm's performance is proportional to the number of candidates that must be tested, bridging improves performance because the start and end attribute constraints are pushed down in the algorithm. However, if only short paths are mined, but long explanation templates are desired (i.e., n>21), then the number of candidates exponentially increases with the length. Thus, for some length n, it is then no longer beneficial to bridge paths.

Inference Engine Handling Missing Data

Thus far we have considered those explanations that can be expressed solely in terms of the data stored in the database. Unfortunately, real databases are typically not perfectly curated. Information may be missing from the database, or relationships may not be recorded. For example, consider a nurse in a hospital who works directly with a doctor. When a patient has an appointment with the doctor, the appointment is recorded in the database, and we can use Explanations Templates to explain the doctor's accesses. Unfortunately, appointments are typically only scheduled with the doctor and not with the nurse. Thus, we cannot explain why the nurse accessed the patient's record, even though the access is appropriate.

To explain these types of accesses, the present techniques are able to access and manage "missing" data in the database. One common type of missing data are those relationships between users of the database. While a database may store information such as the department each user works in, additional information may still be needed to explain accesses. We hypothesize that information used to explain an access such as an appointment often is stored in the database (e.g., an access log) with a reference to a single user, but that information can be used to explain why many other users access the data. Thus, if the database stored relationships among users, additional accesses could be explained.

By adding this missing data, the algorithms implemented on the system may introduce false positive instances of explanations. As discussed below, we study the precision and recall trade-offs from adding missing data and show that even when missing data is added, the rate of false positive explanations is low due to the structure of the explanations.

In some embodiments, the techniques determine relationships between users of a database by analyzing user access patterns. In general, users who work together often access the same data. For example, we expect a nurse and a doctor who work together to often access the same medical records. Using the log of accesses, we can form collaborative groups of users who access the same data often and use these groups to explain more accesses. For example, an explanation why the nurse accesses the patient's medical record could be described as follows: the nurse accesses the patient's medical record because the nurse works with the doctor and the doctor has an appointment with the patient.

Next, we outline one possible approach to construct these collaborative groups that we found to be effective for our data set. However, we note that there has been extensive work on clustering and alternative approaches are possible. In general though, we treat these algorithms as a black box that produces a set of relationships between users of the database. Once this data is plugged into the database, explanation mining algorithms incorporate the information to find additional supported templates. For example, the present techniques may include extracting collaborative groups Extracting Collaborative Groups Given a log of accesses that records which users access which data, the system may include a model of the relationship between database users using a graphical structure, similar to that by Chen et al. Let a node in the graph represent a user. An edge exists between two users if the users access the same data. The system may assign weights to the edges to signify the strength of the users' relationship. To do this for a log of accesses that occur between some start and end time that has m patients and n users, the system may construct an m×n matrix A. The index A[i, j] represents the inverse of the number of users (including user j) that accessed patient i's record. More formally, if user j does not access i's record, then A[i, j]=0, else:

$$A[i,j]=1/\#\text{users who accessed patient } i\text{'s records}$$

The weight of an edge between user $u_1$ and user $u_2$ can be found in W [$u_1$, $u_2$] where W=$A^T$A. Intuitively, W [$u_1$, $u_2$] represents the similarity of two users' access patterns, relative to how often a particular record is accessed. This approach need not adjust the weight depending on the number of times a user accesses a specific record, but rather may only consider if a user accesses the record. A node's weight is defined as the sum of the weights of the edges that are connected to the node.

Given the graphical model, we can directly apply weighted graph clustering algorithms. Specifically, we use a graph clustering algorithm that attempts to maximize the graph modularity measure. Intuitively, optimizing for the graph modularity measure attempts to maximize the connections (and weights) for nodes within a cluster and minimize the connections between nodes that reside in different clusters.

After running the clustering algorithm once, the algorithm outputs a set of clusters and an assignment of users to clusters. The system may recursively apply the clustering algorithm on each cluster to produce a hierarchical clustering. Intuitively, clusters produced at the lower levels of the hierarchy will be more connected than clusters produced at higher levels. Discussed below, we show how this relationship impacts the precision and recall of explaining accesses.

Example 4.1

Figure 7:
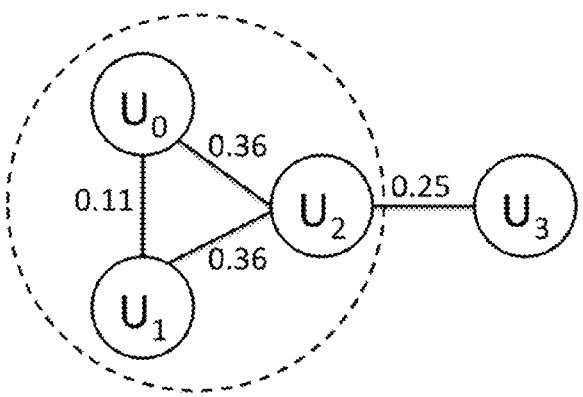
FIG. 7 illustrates an example log of accesses (per patient) and the associated graphical representation with clustering, in accordance with an example.

Consider the log of accesses in FIG. 7 that lists which users have accessed which patient's medical records. From the log, we can construct the matrix A. For example, A[patient A, user 0]=⅓ since three users accessed patient A's record. After evaluating W=$A^T$A, we find the edge weights that are labeled on the graphical representation. After running the clustering algorithms, users 0, 1 and 2 are assigned to the same cluster.

After clustering, an additional table Groups (Group_Depth, Group_id, User) is created in the database. By applying a self-join on this table, the mining algorithms implemented on the system can use these groups to explain additional accesses.

Example 4.2

Nurse Nick's access of Alice's record in FIG. 1 occurred because Nick works with Dave, and Dave has an appointment with Alice. The corresponding explanation template is expressed as follows:

SELECT L.lid, L.Patient, L.User, A.Date, G1.User
FROM Log L, Appointments A, Groups G1, Groups G2
WHERE L.Patient=A.Patient
   AND A.Doctor=G1.User
   AND G1.Group_id=G2.Group_id
   AND G2.User=L.User Experimental Evaluation To test our ideas, we conducted an extensive experimental study using a real access log and database from the CareWeb system at the University of Michigan Health System. Our experiments aim to answer the following questions:

Do explanations exist in real databases? Example 2.1 occur in the real hospital database and can explain over 94% of the accesses in the log.

What missing information can be added to the database? Is this information useful for producing explanations? Using the algorithm described in herein, we were able to find real-life collaborative groups, including the Michigan Cancer Center and the Psychiatric Services offices. After extending the database to include these collaborative groups, we were able to explain many more accesses.

Can systems mine explanation templates efficiently? We measure the performance of the one-way, two-way and bridged algorithms and find they are able to discover explanation templates automatically and efficiently. Moreover, the bridging optimization can improve performance in particular cases.

How effective are the mined explanation templates at correctly classifying future accesses? We measure the precision and recall of the mined explanations and find that shorter explanations provide the best precision, but moderate recall. Longer explanations, including those that use the group information, can be used to improve recall.

Is the same set of explanation templates mined over time? We find that the set of explanation templates discovered by the mining algorithm is relatively stable across time.

Implementation & Environment

In an example implementation, the system was executed as a Python layer on top of PostgreSQL3 system. The layer constructed the paths from the schema and executed the queries on the database to determine an explanation's support. Clustering was performed with a Java implementation of the graph modularity algorithm implemented on the system. The experiments were executed on a dual core CPU with 4 GB of RAM, running Red Hat Linux, providing some of the hardware for the system.

Data Overview

For this example implementation, an extensive experimental study was conducted using data from the University of Michigan Health System. This is believed to be the first study to combine information from an access log with other information stored in a hospital's database for the purpose of explaining data accesses.

In the implementation, a log containing one week's worth of data accesses was used, as was de-identified data about the patients whose medical records were accessed during this period of time. The additional data includes: (data set A) Appointments, Visits, Documents, and (data set B) Labs, Medications and Radiology. Information for these tables was extracted from the weeks around the time of the access. The system may also be given descriptive codes describing which users worked in which departments.

The richness of the data set allows us to mine many different types of explanations. The log contained approximately 4.5 M accesses, 124 K distinct patients, and 12 K distinct users. The number of distinct user-patient pairs is approximately 500 K, which gives a user-patient density of |user–patient pairs|/|users|×|patients|=0.0003. To determine the reason for an access, we received data about approximately 51 K appointments, 3 K visits, 76 K documents produced, 45 K lab records, 242 K medication records, and 17 K radiology records. For example, the Appointment table contains a record for each appointment, including the patient, the doctor, and the date. The Medications table contains a record for each medication order, including the patient, the person who requested the medication, the person who signed for it, and the person who administered it.

When we started the study, we initially requested the Appointments, Visits, and Documents tables, in addition to the log. However, after some preliminary analysis, we discovered that a large proportion of the unexplained accesses were by users who worked in departments that provide services throughout the hospital (e.g., radiology, pathology, and pharmacy). Users in these departments often do not have appointments with patients. However, there is often an explicit request recorded in the database. Therefore, we expanded the study to also include the Labs, Medications, and Radiology tables, which maintain a record for each such request.

Results

Explanations in a Real Data Set

Our first set of experiments tests the fundamental hypothesis that accesses in the log can be explained using data stored elsewhere in the database.

Figure 8:
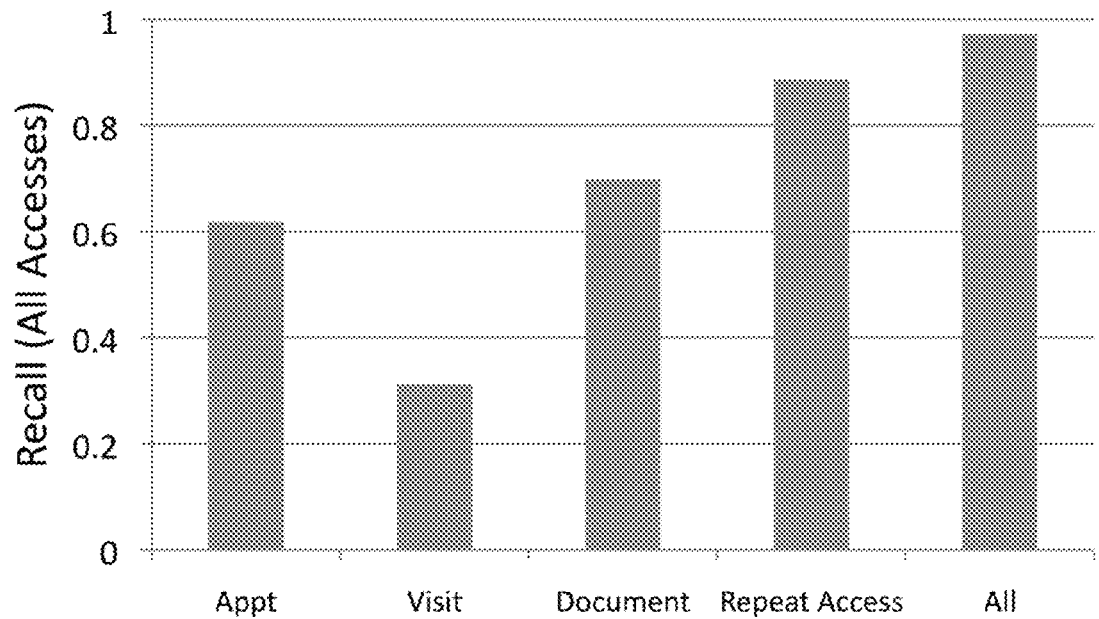
FIG. 8 is a plot of frequency of events in the database for all accesses, in accordance with an example.

We began by measuring the proportion of accesses in the log pertaining to a patient such that the patient had some type of event recorded elsewhere in the database. In particular, we started by measuring the proportion of patients who had an appointment (Appt), visit, or document produced (Doc). FIG. 8 shows the frequency of these events in the log. (The recall of Appointment would be 1.0 if every patient whose record was accessed also had an appointment with someone listed in the database.) As expected, many patients had an appointment with someone in the hospital system or had a document produced (e.g., a doctor's note added to the file). Additionally, a majority of the accesses can be categorized as repeat accesses, meaning that the same user is accessing the patient's record for an additional time. When we combined all these events together, approximately 97% of all accesses corresponded to a patient who had some type of event in the hospital system.

Figure 9:
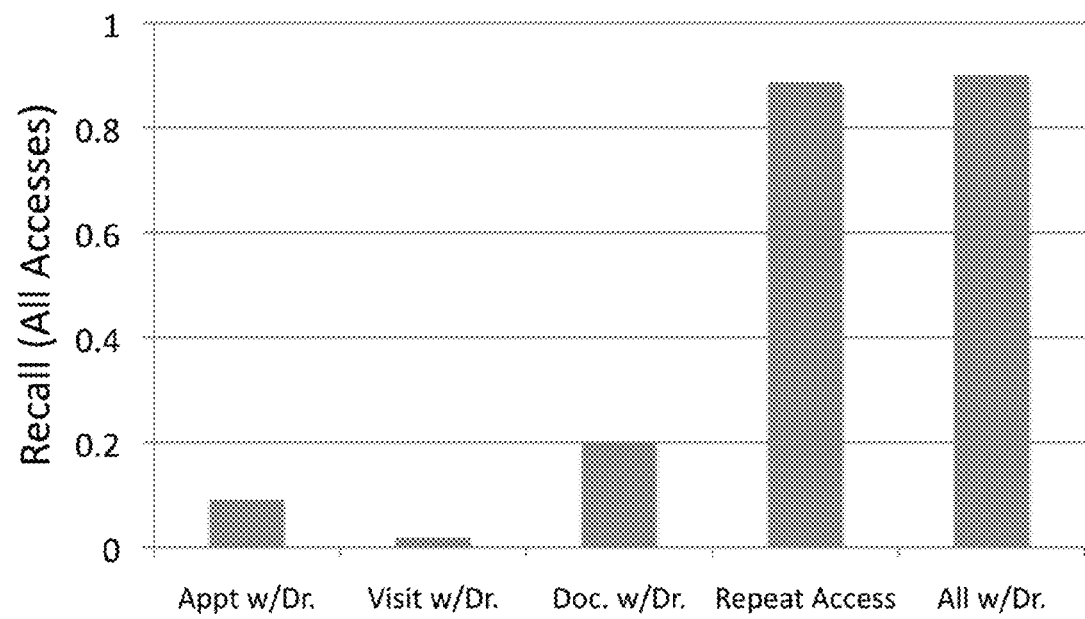
FIG. 9 is a plot of hand-crafted explanations recall for all accesses, in accordance with an example.

Of course, these events do not constitute explanations since they do not necessarily connect the patient whose record was accessed to the specific user who accessed the record. (For example, a patient may have an appointment listed, but it may not be with the person who accessed her record.) We hand-crafted a simple set of explanation templates, based on common reasons for medical records to be accessed, that test if the patient: (i) has an appointment with the specific doctor who accessed the record, (ii) has a visit with the doctor, (iii) has a document produced by the doctor, or (iv) the access was a repeat access. FIG. 9 shows the recall for the explanations (i.e., proportion of the log records explained). While the repeat accesses can still explain a majority of the accesses, the recall of the other explanations is lower. This result is expected because the appointments, visits and documents produced typically only reference the primary doctor in charge of the patient's care. Therefore, using these basic explanation templates, we cannot explain why a nurse accesses a medical record. Even with this lower recall, these explanation templates can still explain 90% of the accesses.

Repeat accesses make up a majority of the log. At the same time, it is more challenging and interesting to explain why a user accesses a medical record for the first time. To do this, we analyzed all of the first accesses in the log, which are those accesses where a user accesses a patient's medical record for the first time. (Notice that since we only have a subset of the log, some accesses that are actually repeat accesses appear to be first accesses.)

Figure 10:
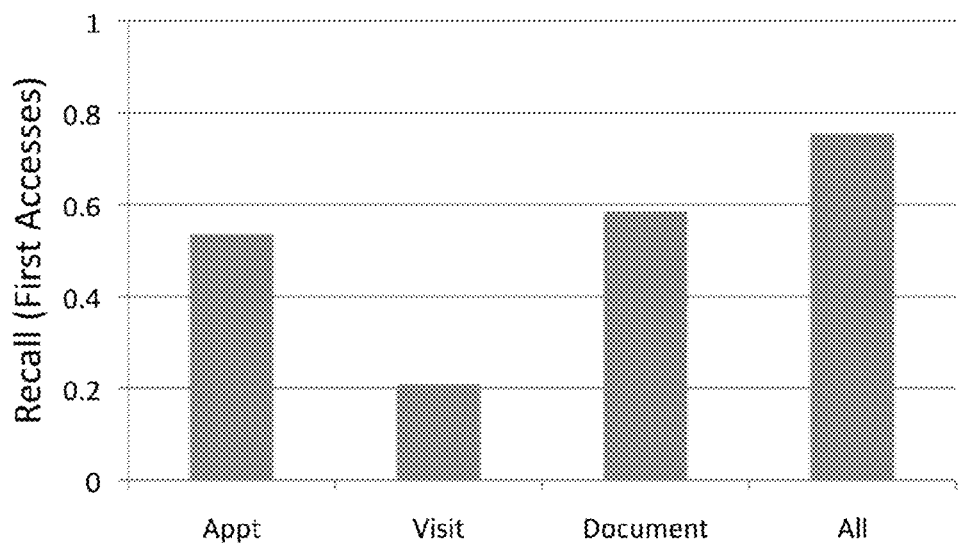
FIG. 10 is a lot of frequency of events in the database for first accesses, in accordance with an example.
Figure 11:
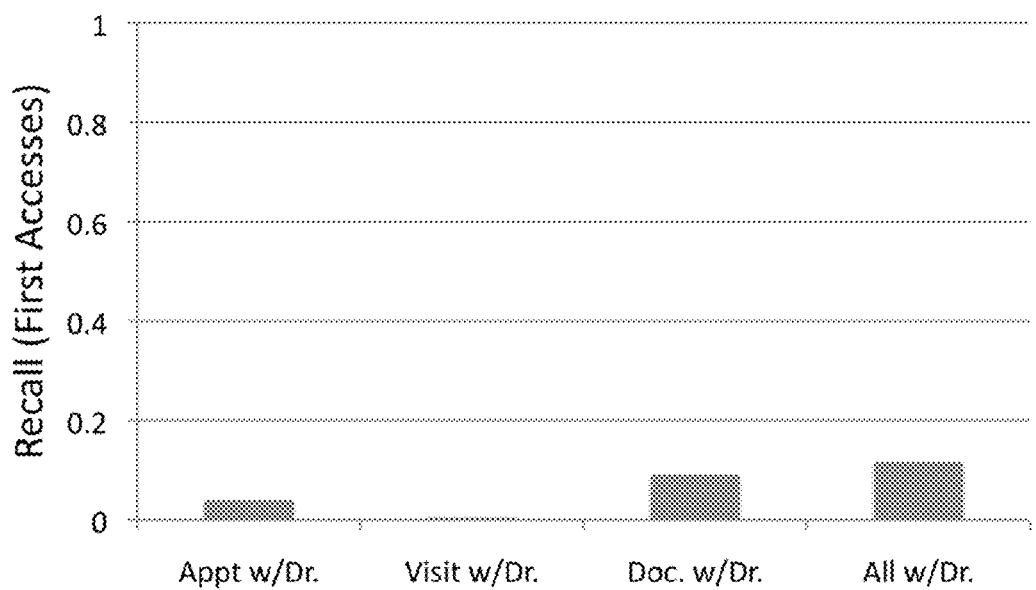
FIG. 11 is another plot of hand-crafted explanations recall for the first accesses of FIG. 10, in accordance with an example.

FIGS. 9 and 10 show the recall for the events and explanation templates given only the first accesses. The explanation templates for appointments, visits and documents produced can explain approximately 11% of the first accesses. Ideally, we should be able to explain approximately 75% of the first accesses since we have information on the patients referenced by these accesses. For the remaining 25% of the accesses, we have no information for those patients and therefore cannot explain why their records are accessed. These unexplained accesses are in part due to our incomplete data set. For example, appointments outside of our week-long timeframe were not extracted.

It is also possible, in some examples, to improve recall by adding missing data, and also by mining additional explanation templates.

Dealing with Missing Data

When a patient has an appointment, the appointment is scheduled with the doctor. However, the nurses who work with the doctor also typically access the patient's medical record. For this reason, we could only explain 11% of the first accesses, even though we have information for 75% of the first accesses. To improve recall, we applied the algorithm to cluster users who access similar medical records using the first six days of accesses in the log. We added these collaborative groups to the database.

Figure 12:
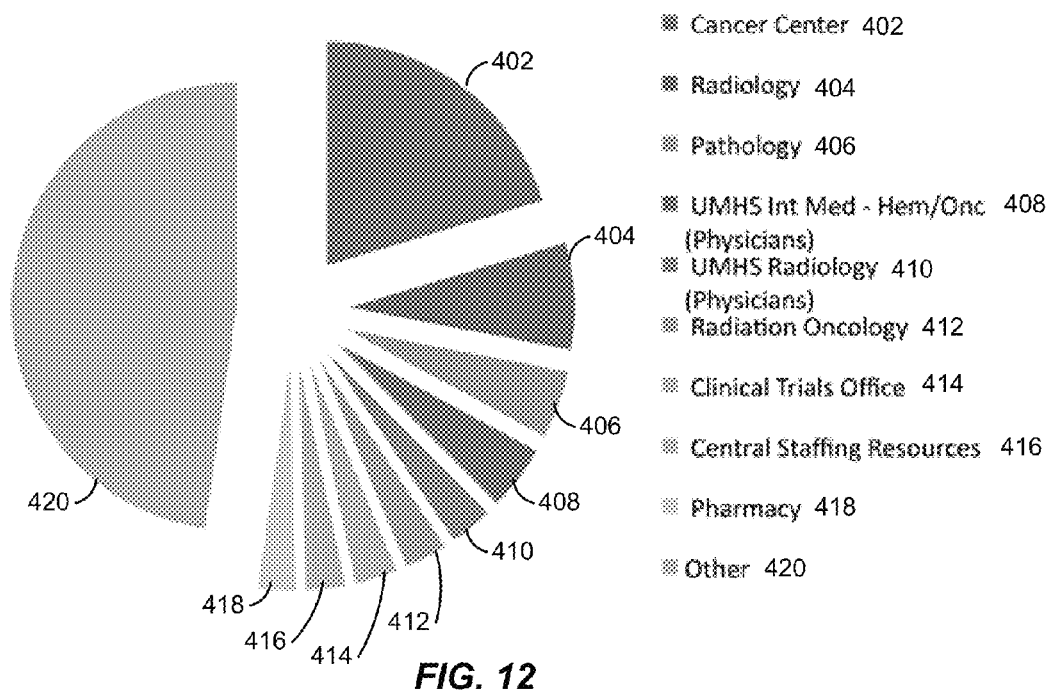
FIG. 12 is a pie chart showing a collaborative group I, in accordance with an example.
Figure 13:
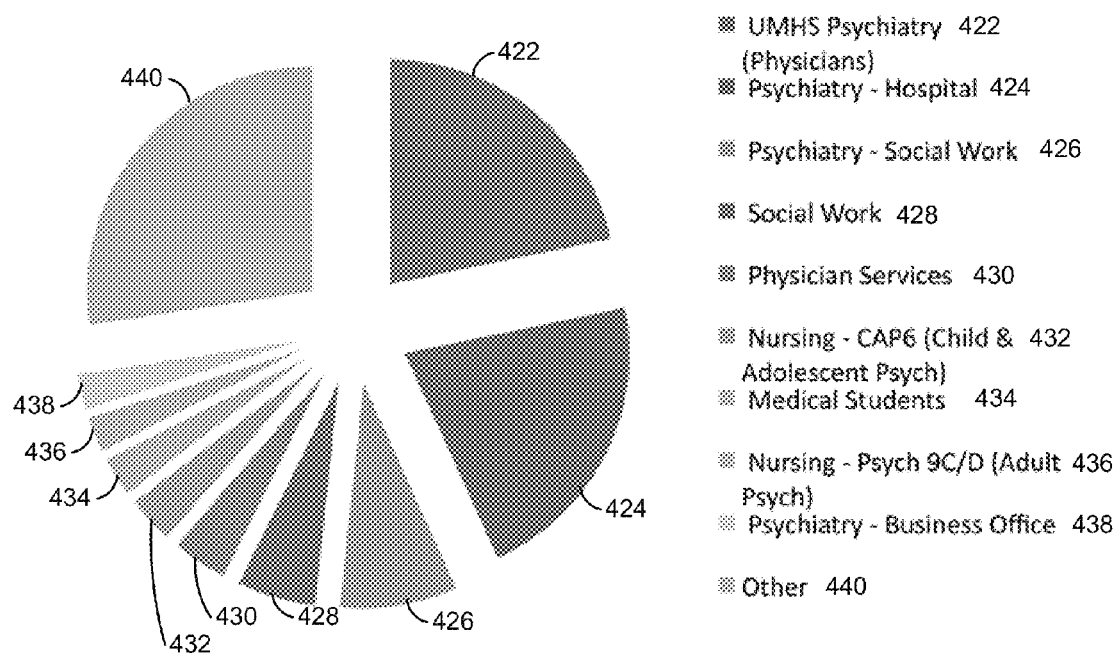
FIG. 13 is a pie chart showing a collaborative group II, in accordance with an example.

A manual examination of the resulting collaborative groups indicates that the process was successful. For example, FIGS. 12 and 13 show the break-down by department codes of two of the 33 toplevel groups produced. The first group (402-420) contains users who work in the Cancer Center. The second group (422-440) contains users who work in psychiatric care.

Interestingly, department codes themselves do not directly coincide with collaborative groups. For example, the Medical Students department code appears in the psychiatric care collaborative group. This makes sense because certain medical students were rotating through the psychiatric care area during the week when our log was collected, and they accessed the associated patients' medical records. However, medical students change rotations on a regular basis. This indicates that it would be incorrect to consider all medical students as their own collaborative group. It also indicates that we must update the collaborative groups from time to time in order to capture the dynamic collaboration patterns within the hospital system.

Our goal in extracting collaborative groups is to improve the recall of explanations (i.e., the number of accesses that can be explained). As a baseline, we could assign all users to a single group; doing this, we are able to explain the 75% of accesses for which there is a corresponding event.

However, this approach has the consequence of potentially providing spurious false positive explanations if the two users are not actually part of a collaborative unit. To measure the tradeoff between adding data to improve recall and introducing false positives, we performed a simple experiment. For the purposes of this experiment, we constructed a fake log that contains the same number of accesses as the real log. We generated each access in the fake log by selecting a user and a patient uniformly at random from the set of users and patients in the database. (Because the user-patient density in the log is so low, it is unlikely that we will generate many fake accesses that "look" real.) We then combined the real and fake logs, and evaluate the explanation templates on the combined log.

We define recall to be the proportion of real accesses returned by an explanation template from the set of all real accesses (Recall=|Real Accesses Explained|/|Real Log|). We define precision to be the proportion of real accesses that are in the set of all accesses returned (Precision=|Real Accesses Explained|/|Real+Fake Access Explained|). The normalized recall, applied by the system, may be the proportion of real accesses returned by an explanation template from the set of accesses we have information on (Normalized Recall=|Real Accesses Explained|/|Real Accesses With Information|). The normalized recall takes into account the fact we have a partial data set. In an ideal world, our explanation templates would observe precision and recall value close to 1.0.

Figure 16:
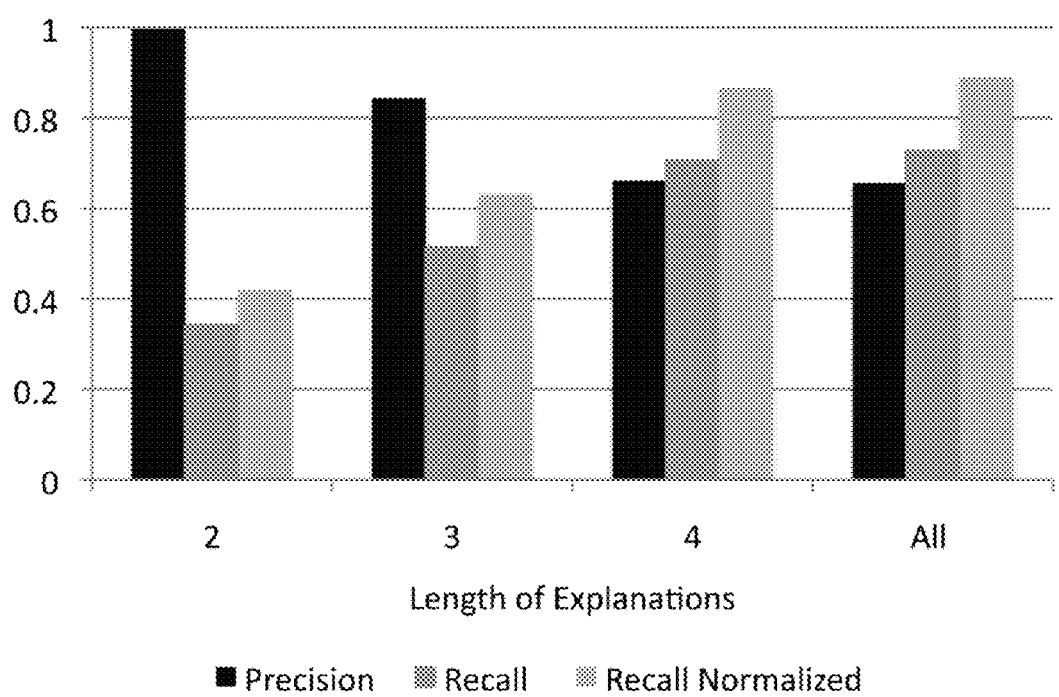
FIG. 16 is a plot of mined explanations predictive power, in accordance with an example.

After generating collaborative groups, the system ended up with an 8 level hierarchy of groups. Then the Groups table was created. Using hand-crafted explanation templates that capture the semantics that a nurse accesses the medical record because the nurse works with the doctor and the doctor has an appointment, visit or produced a document with the patient (e.g., Example 4.2), the system was used to measure the precision, recall and normalized recall. FIG. 16 shows the results for the groups at different levels of the clustering hierarchy using the seventh day's first accesses from the log. Depth 0 captures the naive approach of placing every user in a single group. Additionally, we included the hand-crafted explanation template that captures the idea that a user accesses the medical record because another user in with the same department code has appointment, visit or produced a document with the patient (i.e., explanation (B) from Example 2.1).

As expected, with top-level groups in the hierarchy (Depth 1), the recall was highest and the precision was lowest. Using only appointments, visits and documents produced the system was able to explain approximately 34% of first accesses (41% when normalized for day seven where we have information on 81% of the accesses). As the system examined lower levels in the hierarchy, the recall decreased, but the precision increased because the connections between users in these groups were stronger.

We also found that the explanations based on collaborative groups outperformed explanations based on department codes. This is to be expected due to the multi-disciplinary teams in the hospital. (For example, a pediatrics doctor is labeled Pediatrics, while the nurse is labeled Nursing-Pediatrics. Medical students are labeled Medical Students regardless of their current rotation.)

Mining Explanations

The next set of experiments measured the performance of the mining algorithms. We ran the algorithms, using an example system, on the first accesses from the first six days of the log, with the combined data sets A and B, and the added group information. Based on an initial study, we set the support threshold to 1%. (A support threshold of 1% was sufficient to produce all of the explanation templates that we constructed by hand except one template where a doctor has a visit with a patient, which had a very small support.) We restricted the size of templates to T=3 tables, in the system. We allowed self-joins on the Groups.Group_id attribute and the department code attribute, in the system. As a result, explanations could be of length 4 (the length corresponds to the number of joins in the path). The algorithms utilized the optimizations described herein. Due to how the data was extracted, data set B identifies users with a key audit_id, and data set A identifies users with a caregiver_id. The system used a mapping table to switch from one identifier to the other. Thus, to deal with the slight difference in how the data was extracted, in an example, the system did not count this added mapping table against the number of tables used.

Figure 15:
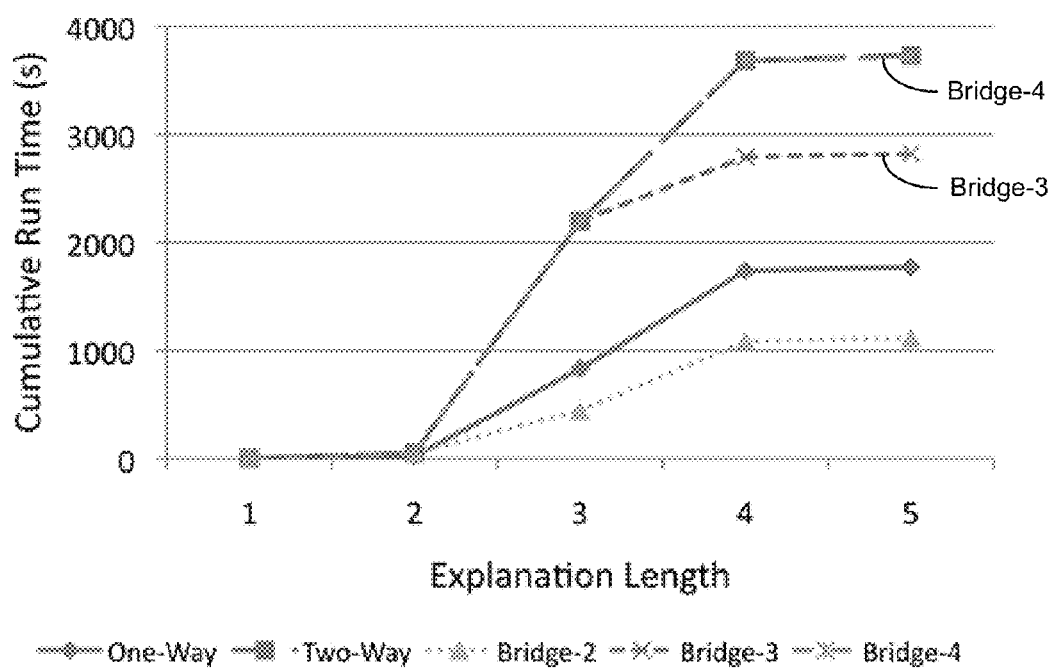
FIG. 15 is a plot of performance of mining algorithms applying one-way and two-way mining algorithms, in accordance with an example.

We evaluated the algorithms based on their performance and their ability to find the hand-crafted explanation templates we previously constructed. FIG. 15 shows the cumulative run time of the various algorithms by path length. Bridge-1 indicates that we used paths up to length l for bridging. For our experimental setup, the Bridge-2 algorithm was the most efficient because it pushes the start and end constraints down in the algorithm. The one-way algorithm was faster than the two-way algorithm because the two-way algorithm considers more initial edges. Without optimizations described herein, the run time may increase by many hours.

Each algorithm produced the same set of explanation templates. Moreover, it is worth noting that our mining algorithms were able to discover all the supported hand-crafted explanation templates we described in the paper such as appointments with doctors, appointments with users that work in the same department, and appointments with users that are in the same group.

Predictive Power of Explanations

Figure 14:
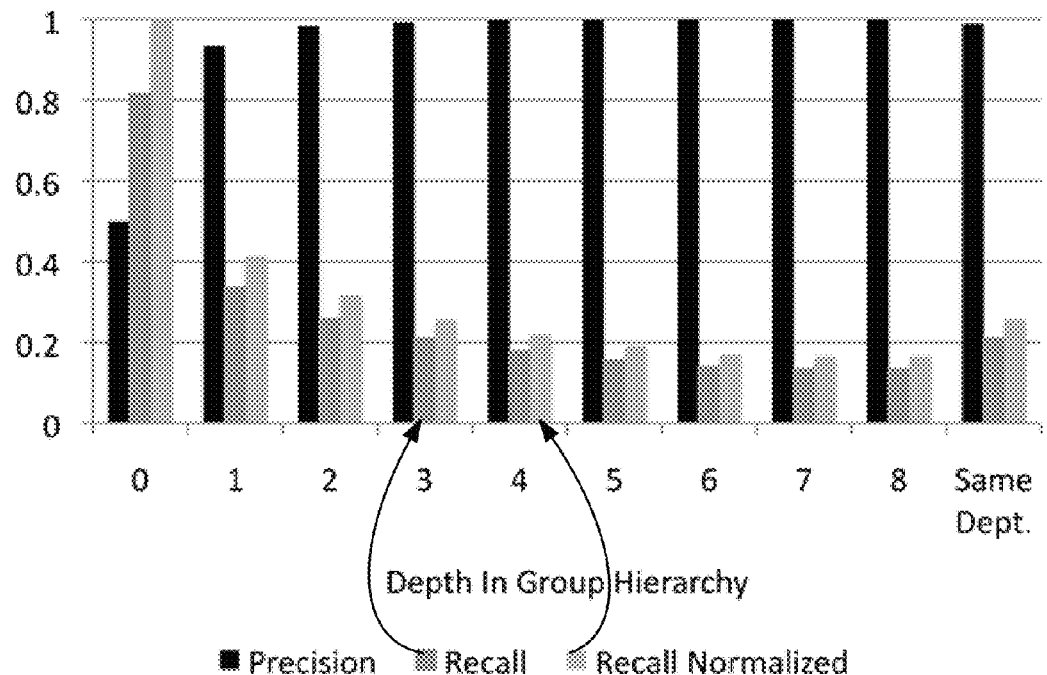
FIG. 14 is a plot of group predictive power for a data set, in accordance with an example.

Using the explanation templates mined from the first six days of accesses, we tested the predictive power of the explanation templates, applied by the system, on the seventh day of accesses using the same fake log that was described above. The goal is to determine if the mined explanation templates can correctly explain real accesses, while not spuriously explaining fake accesses. FIG. 16 shows the results for explanations of various lengths, and the results when all of the explanations are tested together (All). Explanation templates of length two have the best precision, while the recall is approximately 34% (42% normalized). These short explanation are those explanation like explanation (A) from Example 2.1, where the doctor has an appointment with the patient. The precision is high for these explanations because it is very unlikely that, for example, a fake access corresponds to an actual appointment. We believe this is a result of the user-patient density being so small. It is also important to point out that the recall for these length-two explanation templates is higher when data set A and B are combined compared to when only data set A is included in FIG. 14 (the recall increases from 13% to 34% when analyzing the accesses for day seven). This change in recall shows that as more data is added to the database, we can explain additional accesses. With a complete data set, we argue that we can explain more accesses.

As the explanation templates get longer, including self-joins and use group information, the recall increases to approximately 73% (89% when normalized) while the precision drops. The precision drops since it is more likely that a fake access corresponds, for example, to an appointment with a user that is in the same group of the user who accesses the record. When all the explanations are combined and tested together, we find the recall and precision only change slightly from the length-four explanation templates because the longer explanations typically are more general versions of the shorter explanations. Therefore, the longer explanation templates explain most of those accesses explained by the shorter explanation templates. For example, template (B) from Example 2.1 explains all those accesses explained by template (A).

We analyzed the department codes for which we could not explain the largest number of accesses. The top four departments were: Nursing-Vascular Access Service, Anesthesiology, Health Information Management, and Paging & Information Services. The users in the vascular access service typically assist with IVs. Therefore, it makes sense that the explanation templates could not explain their accesses because these users likely work with many different types of patients and many different types of hospital employees, and our data set does not explicitly record why these nurses treated the patient. Using this observation, one may create additional explanation templates or add more missing data, e.g., using the system. As described herein the system For example, one possible decorated explanation template we could create could be: the user works in the vascular access service and only accesses nonsensitive parts of the patient's medical record such as the patient's name and room number.

For the evaluation, we used group information from any depth in the hierarchy. However, we observe that not every event type should use the same depth. For example, when only data set A was used, we had a precision of approximately 93%, however when data set B was included, the precision dropped to 66%. Therefore, group information at one depth may be sufficient to explain an access with an appointment, but group information at another depth may be necessary to explain accesses with medication information to attain a desired level of precision. In the future, we will consider how to mine decorated explanation templates that restrict the groups that an explanation can use to better control the precision.

Stability of Explanations

Lastly, we measure the stability of the explanation templates that are mined over different time periods to determine if there exists a set of consistently occurring explanation templates. To do this, we ran the mining algorithms on different subsets of the log: days 1-6, day 1, day 3 and day 7. Table 1 shows the number of explanation templates produced per time period. For our data sets, the number of explanations that are produced is small enough for an administrator to manually analyze and approve those semantically correct explanations. Moreover, there is a set of common explanation templates that occur in every time period. Therefore, we believe the explanation templates mined represent generic reason why medical records are accessed.

TABLE 1

Number of explanations mined

| | # Explanation Templates | | | | |
| --- | --- | --- | --- | --- | --- |
| Length | Days 1-6 | Day 1 | Day 3 | Day 7 | Common Templates |
| 2 | 11 | 11 | 11 | 12 | 11 |
| 3 | 241 | 257 | 231 | 268 | 217 |
| 4 | 25 | 25 | 25 | 27 | 25 |

We did observe a small difference in the explanations produced from time period to time period. For example, on day 7, a twelfth length-two explanation template was added because there were more accesses corresponding to visits. We found larger variability in length-three explanations. This variation occurred from those explanation templates that had paths that connected two different event types. For example, the path from radiology information to medication information would occur frequently during some time periods, but would not occur frequently during others.

Some conventional techniques have focused on a somewhat related problem of DBMS or SQL log auditing. In this case, logs are collected at the level of the DBMS recording the text of all SQL queries and updates; most commercial DBMSs now support this form of logging. Unfortunately, in contrast to application-level auditing, with such conventional systems it is non-trivial to determine which logged queries accessed particular portions of the database, or particular records, and used these records in non-trivial ways.

Various models and systems have been proposed to address this problem for audit logs collected at the level of the DBMS. For example, anomaly-based intrusion and misuse detection have been studied in the past. In the electronic health records domain, Chen et al. study how to detect anomalous insiders by analyzing an access log in a real hospital system; they detect anomalous users by measuring the deviation of each user's access pattern from that of his neighbors. This work considers the user to be the unit of suspiciousness, deciding whether or not a user is behaving in an unexpected way.

In contrast to these limited conventional techniques, the present techniques consider individual accesses and explain why each access occurs. This approach may be more appropriate in many instances, for example, where hospital employees are generally well-behaved, but in some isolated cases they inappropriately access information (e.g., the Britney Spears and Barack Obama cases). In addition, the present techniques are able to produce easily interpretable results, while the output of the anomaly detection mechanism does not clearly explain why a user is suspicious.

Other work, by Malin et al., proposed learning access control policies from EHR access logs. They used a data-driven approach to determine relationships between users and departments in the hospital. Using these relationships, for example, the system could apparently determine the probability with which a patient's medical record will be accessed by a surgeon after it is accessed by an emergency room physician.

The mining algorithms presented in the present techniques have numerous distinctions over such previous work on pattern mining. Some of these differences include (i) that the present techniques are mining connected paths between a start and end attributes in the schema, where the classical problem mines item sets; (ii) the metric for frequency (support) is determined by the number of accesses in the log that are explained by the template—therefore, every path we consider must reference the log; (iii) the structure of the patterns that are mined and where the data is stored differs from the classical problem (for instance, the templates represent logical expressions that data in the database must satisfy, whereas in contrast, the classical problem learns relationships between actual values); and (iv) the data may be stored across multiple tables in the database, rather than in a single file of transactions.

In short none the conventional techniques are able to directly solve the problem of explaining accesses in a database.

In contrast, the present techniques provide for automated explanation-based auditing. We observe that electronic health records systems collect access logs. While this information is useful to explain who has accessed a patient's medical records, patients will likely also want to understand why their medical records were accessed. To address this problem, a framework is provided that attempts to generate an explanation for why an access occurred. The techniques may be based on a fundamental observation that accesses in specific classes of databases occur for a reason and the reason can be inferred from data in the database. The techniques included modeling an explanation as a path that connects the data that is accessed to the user who accessed it, by way of data in the database. Producing explanations for a large database can be time consuming. Instead, a system provides algorithms to automatically mine explanations from the data. Additionally, the techniques also showed how group information derived from access patterns could be added to the database to enhance these explanations. We evaluated our system on a real log and data set from the University of Michigan Health System. Using our model, we can explain over 94% of the accesses.

Figure 17:
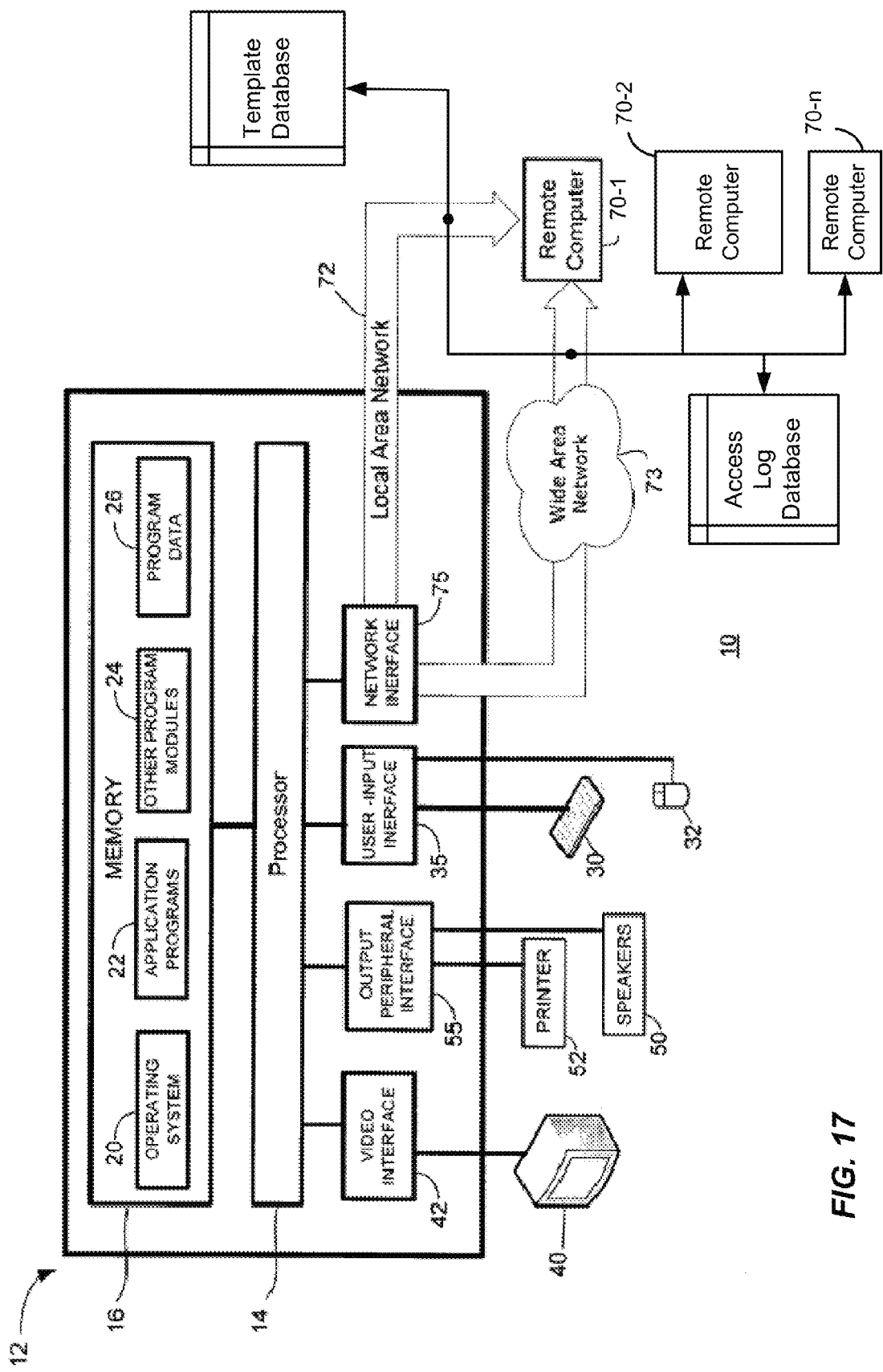
FIG. 17 illustrates a block diagram of a computer system that may operate in accordance with an example.

In the example embodiment illustrated in FIG. 17, a computer system for performing automatic explanation-based auditing of medical records data. The techniques described may be coded, in software, hardware, firmware, or combination thereof, for execution on a computing device such as that illustrated in FIG. 17. Generally, FIG. 17 illustrates an example of a suitable computing system environment 10 to interface with a medical professional or other user to enter and access medical records data and to audit interactions with that data. It should be noted that the computing system environment 10 is only one example of a suitable computing environment and is not intended to suggest any limitation as to the scope of use or functionality of the method and apparatus of the claims.

With reference to FIG. 17, an exemplary system for implementing the blocks of the claimed method and apparatus includes a general-purpose computing device in the form of a computer 12. Components of computer 12 may include, but are not limited to, a processing unit 14 and a system memory 16. The computer 12 may operate in a networked environment using logical connections to one or more remote computers, such as remote computers 70-1, 70-2, . . . 70-n, via a local area network (LAN) 72 and/or a wide area network (WAN) 73 via a modem or other network interface 75. These remote computers 70 may include other computers like computer 12, but in some examples, these remote computers 70 include one or more of a (i) hospital patient information system, including hospital patient records, (ii) a pharmacy management system, including pharmacy data for drugs and drug interactions and (in some examples) patient prescription information, and (iii) a hospital management system that stores data related to hospital policy for patient treatment. Also connected to the computer system 12 through either or both the local area network 72 and wide area network 73 is a Template Database containing Explanation Templates and an Access Log Database containing User Access Data, such as that partially illustrated in FIGS. 4A-4C. The Log Database may include information of visits, appointments, documents, labs, medications, patients, radiology, etc. each stored in a different table with the Log Database.

Computer 12 typically includes a variety of computer readable media that may be any available media that may be accessed by computer 12 and includes both volatile and nonvolatile media, removable and non-removable media. The system memory 16 includes computer storage media in the form of volatile and/or nonvolatile memory such as read only memory (ROM) and random access memory (RAM). The ROM may include a basic input/output system (BIOS). RAM typically contains data and/or program modules that include operating system 20, application programs 22, other program modules 24, and program data 26. The computer 12 may also include other removable/non-removable, volatile/nonvolatile computer storage media such as a hard disk drive, a magnetic disk drive that reads from or writes to a magnetic disk, and an optical disk drive that reads from or writes to an optical disk.

A user may enter commands and information into the computer 12 through input devices such as a keyboard 30 and pointing device 32, commonly referred to as a mouse, trackball or touch pad. Other input devices (not illustrated) may include a microphone, joystick, game pad, satellite dish, scanner, or the like. These and other input devices are often connected to the processing unit 14 through a user input interface 35 that is coupled to a system bus, but may be connected by other interface and bus structures, such as a parallel port, game port or a universal serial bus (USB). A monitor 40 or other type of display device may also be connected to the processor 14 via an interface, such as a video interface 42. In addition to the monitor, computers may also include other peripheral output devices such as speakers 50 and printer 52, which may be connected through an output peripheral interface 55.

Generally, the techniques herein may be coded in the Python language or any other computing language for execution on computer 12. For example, once an explanation-auditing program is loaded on to computer 12, the program may be executed on Access log data or other database data containing medical records, and databases containing Explanation Templates. Such data may be loaded on to any of the computer storage devices of computer 12, for example by accessing one or more of the remote computers 70-1, 70-2, . . . 70-n. Once generated, the auditing algorithms applied herein, which may take the form of a large set of if-then conditions, may then be coded using any general computing language for test implementation. For example, the if-then conditions can be capture using C/C++ and compiled to produce an executable, which, when run, provides explanation audits of the user interactions with the system. The output of the executable program may be displayed on a display (e.g., a monitor 40), sent to a printer 52, stored for later use by the computer 12, or offloaded to another system, such as one of the remote computers 70. The output may be in the form of a graph or table indicating the explanation audit.

Figure 18:
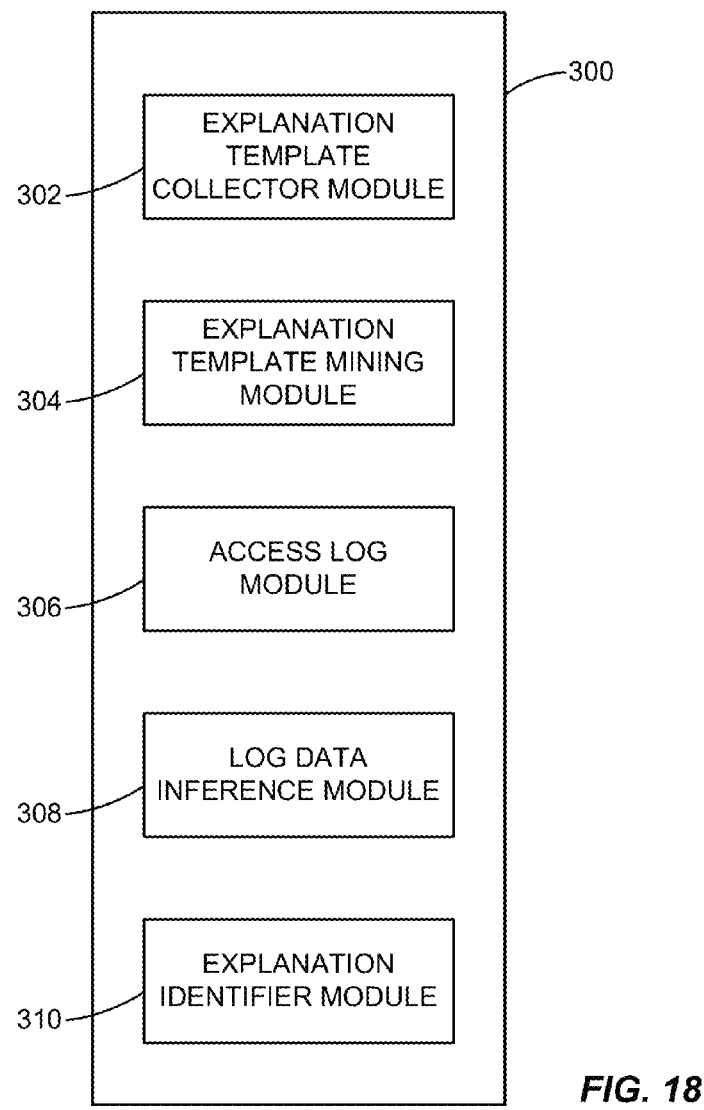
FIG. 18 illustrates a block diagram of an automated explanation auditing system as may be operated on the computer system of FIG. 17, in accordance with an example.

FIG. 18 illustrates an example automatic Explanation Auditing System 300 that may be implemented in the computer system 12 to perform the techniques of the present application, such as the process of FIG. 2. The Explanation Auditing System includes (i) an Explanation Template Collector Module 302, for accessing the Template Database having multiple explanation templates; (ii) an Explanation Template Mining Module 304, to mine those explanation templates to identify a candidate subset for analysis; (iii) an Access Log Module 306, to access an Access Log Database containing log data of user access to records in a records database; (iv) a Log Data Inference Module 308, to infer data not available in the Access Log Database; and (v) an Explanation Identifier Module 310, to identify an explanation for a particular user access.

More generally, the various blocks, operations, and techniques described above may be implemented in hardware, firmware, software, or any combination of hardware, firmware, and/or software. When implemented in hardware, some or all of the blocks, operations, techniques, etc. may be implemented in, for example, a custom integrated circuit (IC), an application specific integrated circuit (ASIC), a field programmable logic array (FPGA), a programmable logic array (PLA), etc.

When implemented in software, the software may be stored in any computer readable memory such as on a magnetic disk, an optical disk, or other storage medium, in a RAM or ROM or flash memory of a computer, processor, hard disk drive, optical disk drive, tape drive, etc. Likewise, the software may be delivered to a user or a system via any known or desired delivery method including, for example, on a computer readable disk or other transportable computer storage mechanism or via communication media. Communication media typically embodies computer readable instructions, data structures, program modules or other data in a modulated data signal such as a carrier wave or other transport mechanism. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, radio frequency, infrared and other wireless media. Thus, the software may be delivered to a user or a system via a communication channel such as a telephone line, a DSL line, a cable television line, a wireless communication channel, the Internet, etc. (which are viewed as being the same as or interchangeable with providing such software via a transportable storage medium).

Moreover, while the present invention has been described with reference to specific examples, which are intended to be illustrative only and not to be limiting of the invention, it will be apparent to those of ordinary skill in the art that changes, additions and/or deletions may be made to the disclosed embodiments without departing from the spirit and scope of the invention.

What is claimed is:

1. A method for identifying an explanation for a user access to records in a records database, the method comprising:
   accessing, using a computer system, a template database containing a plurality of explanation templates, each explanation template corresponding to a potential reason for user access to the records database;
   accessing, using the computer system, log data stored in an access log database and identifying the user access to the records in the records database;
   automatically mining, using the computer system, the plurality of explanation templates to identify candidate explanation templates based on the access log data;
   automatically extracting, using the computer system, an explanation corresponding to the user access to the records in the records database, based on the candidate explanation templates; and
   storing the extracted explanation.

2. The method of claim 1, further comprising a user identifying the log data.

3. The method of claim 1, further comprising mining the plurality of explanation templates to identify a set of frequently used explanation templates as the candidate explanation templates.

4. The method of claim 1, further comprising mining the plurality of explanation templates based on template type.

5. The method of claim 1, further comprising mining the plurality of explanation templates based on the lengths of explanation templates in the template database.

6. The method of claim 1, further comprising mining the plurality of explanation templates based on the number of tables used to construct the log data stored in the access log database.

7. The method of claim 1, further comprising mining the plurality of explanation templates based on the amount of data in the access log database.

8. The method of claim 1, further comprising mining the plurality of explanation templates using a one-way algorithm.

9. The method of claim 1, further comprising mining the plurality of explanation templates using a two-way algorithm.

10. The method of claim 1, further comprising:
    inferring data from missing links between data from the log data; and
    automatically mining the plurality of explanation templates to identify the candidate explanation templates based on the log data and the inferred missing data.

11. The method of claim 1, further comprising:
inferring data from missing links between data from the log data; and
adding the inferred data to the log data.

12. The method of claim 1, further comprising determining the accuracy extracted explanation corresponding to the user access.

13. The method of claim 1, wherein accessing log data stored in the access log database comprising collecting and accessing data real time as the user accesses the records.

14. The method of claim 1, wherein accessing log data stored in the access log database comprising collecting and accessing data previously stored in the access log database.

15. The method of claim 1, wherein the extracted explanation represents at least one connection that begins at the access log database, continues through the access log database and/or the records database, and ends by returning to the access log database.

16. The method of claim 15, wherein the at least one connection begins at data in the access log database describing information that was accessed by the user and wherein returning to the access log database comprises returning to data describing the user who accessed the information.

17. The method of claim 15, wherein the extracted explanation represents a plurality of connection paths through the access log database.

18. The method of claim 1, wherein the log data comprises at least two of patient data, event data, doctor data, and user data.

19. The method of claim 18, wherein at least two of the patient data, event data, doctor data, and user data are stored in different accessible data tables in the access log database.

20. The method of claim 1, wherein the access log database is separate from the computer system and coupled thereto through a network communication link.

21. The method of claim 20, wherein the network communication link is a wired communication link.

22. The method of claim 20, wherein the network communication link is a wireless communication link.

23. The method of claim 1, wherein the template database is separate from the computer system and coupled thereto through a network communication link.

24. The method of claim 23, wherein the network communication link is a wired communication link.

25. The method of claim 23, wherein the network communication link is a wireless communication link.

26. The method of claim 1, wherein the template database is stored on a remote server.

27. The method of claim 26, wherein the access log database is stored on the remote server.

28. The method of claim 1, wherein the records are medical records.

29. The method of claim 1, wherein the records are government records.

30. The method of claim 1, wherein the records are credit card records.

31. The method of claim 1, further comprising automatically detecting misuse of the records by the user, based on the extracted explanation.

32. A user-centric auditing system configured to perform the method of claim 1, wherein the extracted explanation is presented by the auditing system in a natural language format.

33. A computer system configured to perform the method of claim 1.

34. A computer system comprising:
a memory;
a network interface for connecting the computer system to one or more remote network devices; and
a processor having
an explanation template collector module configured to access a template database having multiple explanation templates,
an explanation template mining module configured to automatically mine the multiple explanation templates to identify a candidate subset explanation templates,
an access log module configured to access an access log database containing log data of user access to records in a records database,
a log data inference module configured to infer data not available in the access log database containing the log data of user access to the records in the records database, and
an explanation identifier module configured to automatically identify an explanation for a particular user access to the database.

35. The computer system of claim 34, wherein at least one of the records database, the access log database, and the template database are remote to the computer system and connected to the computer system through the network interface.

36. A user-centric auditing system configured to identify one or more explanations for user access to records in a records database, the auditing system comprising:
a processor; and
a memory storing computer-readable instructions that when executed by the processor cause the auditing system to,
access a template database containing a plurality of explanation templates, each explanation template corresponding to a potential reason for user access to the records database,
access log data stored in an access log database and identify the user access to the records in the records database,
automatically mine the plurality of explanation templates to identify candidate explanation templates based on the access log data,
automatically extract one or more explanations corresponding to the user access to the records in the records database, based on the candidate explanation templates, wherein the one or more explanations are in a natural language format, and
present the one or more explanations in the natural language format to a reviewing user.

37. The user-centric auditing system of claim 36, wherein at least one extracted explanation explains numerous user accesses to the records in the records database.

38. The user-centric auditing system of claim 36, wherein the extracted explanation is determined from a parameterized description string.

39. The user-centric auditing system of claim 36, wherein a plurality of extracted explanations are presented to the reviewing user, wherein the memory further stores computer-readable instructions that when executed by the processor cause the auditing system to present the plurality of extracted explanations in a ranked order.

40. The user-centric auditing system of claim 36, wherein the one or more explanations are suspicious explanations of access to be reviewed by the reviewing user.

41. The user-centric auditing system of claim 36, wherein the one or more explanations are presented to the reviewing user for detecting misuse of the records by the user.

* * * * *

UNITED STATES PATENT AND TRADEMARK OFFICE
CERTIFICATE OF CORRECTION

PATENT NO. : 8,745,085 B2
APPLICATION NO. : 13/589072
DATED : June 3, 2014
INVENTOR(S) : Daniel Fabbri et al.

It is certified that error appears in the above-identified patent and that said Letters Patent is hereby corrected as shown below:

In the Specification

Column 1, immediately after the title, please insert:
--Statement of Government Interest
This invention was made with government support under CNS0915782 awarded by the National Science Foundation. The government has certain rights in the invention.--

Signed and Sealed this
Sixth Day of August, 2019

Andrei Iancu
*Director of the United States Patent and Trademark Office*